United States Patent [19]

Chan

[11] 4,012,519
[45] Mar. 15, 1977

[54] FUNGICIDAL 3-(N-ACYL-N-ARYLAMINO) LACTONES AND LACTAMS

[75] Inventor: David Cheong King Chan, San Francisco, Calif.

[73] Assignee: Chevron Research Company, San Francisco, Calif.

[22] Filed: Nov. 12, 1975

[21] Appl. No.: 631,351

Related U.S. Application Data

[63] Continuation-in-part of Ser. No. 548,660, Feb. 10, 1975, Pat. No. 3,933,860.

[52] U.S. Cl. ............................ 424/274; 260/326.45; 260/326.42; 260/343.6; 424/279
[51] Int. Cl.² ............................................ A01N 9/20
[58] Field of Search ................. 260/326.45, 326.42, 260/343.6; 424/274, 279

[56] References Cited
UNITED STATES PATENTS 3,933,860   1/1976   Chan ........................... 260/326.45

*Primary Examiner*—Lewis Gotts
*Assistant Examiner*—Cary Owens
*Attorney, Agent, or Firm*—George F. Magdeburger; Dix A. Newell; Raymond Owyang

[57] ABSTRACT

3-(N-acyl-N-arylamino)-gamma-lactones, delta-lactones, gamma-lactams and delta-lactams have fungicidal activity.

15 Claims, No Drawings

FUNGICIDAL 3-(N-ACYL-N-ARYLAMINO) LACTONES AND LACTAMS

RELATED APPLICATION

This application is a continuation-in-part of application Ser. No. 548,660, filed Feb. 10, 1975, now U.S. Pat. No. 3,933,860, the disclosure of which is incorporated herein by reference.

DESCRIPTION OF THE INVENTION

The 3-(N-acyl-N-arylamino) lactones and lactams of the invention are represented by the formula (I):

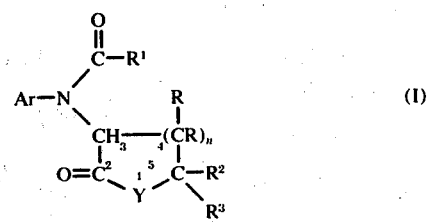

wherein Ar is phenyl or phenyl substituted with 1 to 3 of the same or different substituents selected from fluoro, chloro, bromo, alkyl of 1 to 4 carbon atoms, alkoxy of 1 to 4 carbon atoms or nitro; R is the same or different and is hydrogen or alkyl of 1 to 6 carbon atoms; $R^1$ is phenyl, phenyl substituted with 1 to 3 of the same or different sutstituents selected from trifluoromethyl, trichloromethyl, fluoro, chloro, bromo, alkyl of 1 to 4 carbon atoms, alkoxy of 1 to 4 carbon atoms or nitro, alkyl of 1 to 6 carbon atoms, halovinyl of 1 to 3 of the same or different halogens selected from fluoro, chloro or bromo, or haloalkyl of 1 to 3 carbon atoms and 1 to 5 of the same or different halogens selected from fluoro, chloro or bromo; $R^2$ is hydrogen or alkyl of 1 to 6 carbon atoms; $R^3$ is hydrogen or alkyl of 1 to 6 carbon atoms; $n$ is 1 or 2; and Y is oxygen or N-$R^4$ wherein $R^4$ is hydrogen, alkyl of 1 to 6 carbon atoms, alkenyl of 3 to 6 carbon atoms, phenyl, phenyl substituted with 1 to 3 of the same or different substituents selected from trifluoromethyl, trichloromethyl, fluoro, chloro, bromo, alkyl of 1 to 4 carbon atoms, alkoxy of 1 to 4 carbon atoms or nitro.

Representative alkyl groups which R, $R^1$, $R^2$, $R^3$ and $R^4$ may represent are methyl, ethyl, propyl, isopropyl, n-butyl, t-butyl, pentyl, isohexyl, etc.

Representative halovinyl groups which $R^1$ may represent are 2-chlorovinyl, 2,2-dibromovinyl, trichlorovinyl, etc.

Representative haloalkyl groups which $R^1$ may represent include fluoromethyl, chloromethyl, bromomethyl, dichloromethyl, tribromomethyl, 2-chloroethyl, 1,1,2,2-tetrachloroethyl, perbromoethyl, 3-chloropropyl, etc.

Representative substituted-phenyl groups which Ar, $R^1$ and $R^4$ may represent are 2-trifluoromethylphenyl, 2-fluorophenyl, 2,4-dichlorophenyl, 3,5-dibromophenyl, 4-methylphenyl, 2,6-diethylphenyl, 4-methoxyphenyl, 4-nitrophenyl, 2,6-dimethyl-4-chlorophenyl, etc.

Representative N-$R^4$ groups are amino; alkylamino such as methylamino, ethylamino, isopropylamino, n-hexylamino, etc.; alkenylamino such as allylamino, 3-butenylamino, etc.; and arylamino such as phenylamino, 4-chlorophenylamino, 4-tolylamino, etc.

Preferably Ar is phenyl or phenyl substituted with 1 to 2 of the same or different substituents defined above. More preferably Ar is phenyl or phenyl substituted with 1 to 2 fluoro, chloro, bromo or alkyl of 1 to 4 carbon atoms. Most preferably Ar is 2,6-dialkylphenyl.

Preferably $R^1$ is alkyl of 1 to 6 carbon atoms, phenyl, phenyl substituted with 1 to 2 of the same or different substituents selected from fluoro, chloro, bromo or alkyl of 1 to 4 carbon atoms, or haloalkyl of 1 to 3 carbon atoms and 1 to 2 chloro or bromo. More preferably $R^1$ is haloalkyl of 1 to 3 carbon atoms and 1 to 2 chloro or bromo. Most preferably $R^1$ is chloromethyl or homomethyl.

Preferably R, $R^2$ and $R^3$ are hydrogen.

Preferably $R^4$ is hydrogen, alkyl of 1 to 6 carbon atoms, alkenyl of 3 to 6 carbon atoms, phenyl or phenyl substituted with 1 to 2 fluoro, chloro, bromo or alkyl of 1 to 4 carbon atoms.

Preferably Y is oxygen or alkylamino (N-$R^4$ wherein $R^4$ is alkyl).

Most preferably Y is oxygen.

Preferably $n$ is 1.

A preferred class of compounds represented by formula (I) is that wherein Ar is 2,6-dialkylphenyl, R is hydrogen, $R^1$ is chloromethyl or bromomethyl, $R^2$ and $R^3$ are hydrogen, Y is oxygen and $n$ is 1.

Representative compounds of formula (I) include:
3-(N-acetyl-N-phenylamino)-gamma-butyrolactone
3-(N-propionyl-N-4-chlorophenylamino)-gamma-butyrolactone
3-(N-hexanoyl-N-4-methoxyphenylamino)-gamma-butyrolactone
3-(N-fluoroacetyl-N-2,6-dimethylphenylamino)-gamma-butyrolactone
3-(N-dichloroacetyl-N-2,6-diethylphenylamino)-gamma-butyrolactone
3-(N-3-chloropropionyl-N-3,4-dibromophenylamino)-gamma-butyrolactone
3-(N-benzoyl-N-4-nitrophenylamino)-4-methylgamma-butyrolactone
3-(N-4-chlorobenzoyl-N-2-methoxyphenylamino)-gamma-butyrolactone
3-(N-4-methylbenzoyl-N-3,4-dichlorophenylamino)-4,4-dimethyl-gamma-butyrolactone
3-(N-2,4-dimethylbenzoyl-N-2-fluorophenylamino)-gamma-butyrolactone
3-(N-4-methoxybenzoyl-N-4-methoxyphenylamino)-gamma-butyrolactone
3-(N-propionyl-N-2,6-dimethylphenylamino)-5-methylgamma-butyrolactone
3-(N-benzoyl-N-2,6-diethylphenylamino)-5-ethyl-gamma-butyrolactone
3-(N-chloroacetyl-N-3,4-dichlorophenylamino)-5-hexylgamma-butyrolactone
3-(N-chloroacetyl-N-2,6-dimethylphenylamino)-delta-valerolactone
3-(N-4-bromobenzoyl-N-3-methylphenylamino)-delta-valerolactone
3-(N-acetyl-N-2-propylphenylamino)-delta-valerolactone
3-(N-bromoacetyl-N-2,6-dimethylphenylamino)-6-methyldelta-valerolactone
3-(N-pentanoyl-N-4-nitrophenylamino)-6-hexyldelta-valerolactone
3-(N-dibromobenzoyl-N-4-methoxyphenylamino)-5-methyl-6-methyl-delta-valerolactone
3-(N-acetyl-N-2,6-dimethylphenylamino)-gamma-butyrolactam 3-(N-chloroacetyl-2,6-dimethoxyphenylamino)-
    gamma-butyrolactam
3-(N-benzoyl-N-2-nitrophenylamino)-gamma-
    butyrolactam
1-methyl-3-(N-chloroacetyl-N-2,6-dimethyl-
    phenylamino)-gamma-butyrolactam
1-allyl-3-(N-p-chlorobenzoyl-N-2,6-dimethyl-
    phenylamino)-5-phenyl-gamma-butyrolactam
3-(N-bromoacetyl-N-phenylamino)-1,5-dimethyl-
    gamma-butyrolactam
3-(N-chloroacetyl-N-2,6-dimethylphenylamino)-del-
    ta-valerolactam
3-(N-bromoacetyl-N-2,6-diethylphenylamino)-delta-
    valerolactam
1-methyl-3-(N-chloroacetyl-N-2,6-dimethyl-
    phenylamino)-delta-valerolactam and
1-ethyl-3-(N-bromoacetyl-N-2,6-diethyl-
    phenylamino)-6-methyldelta-valerolactam.

The lactone compounds of the invention may be prepared by alkylating an aniline (II) with an alpha-halo-gamma-lactone or alpha-halo-delta-lactone (III) and subsequently acylating the alpha-(N-arylamino)-gamma-lactone or delta-lactone (IV) with an acyl halide (V) to give the 3-(N-acyl-N-arylamino)-gamma-lactone or delta-lactone product (I), as depicted by the following equations:

one modification of the reaction, a molar excess of the aniline reactant (II) is used as the base, and no additional base is employed. The reaction is conducted in inert polar organic solvents, e.g., apolar diprotic solvents such as dimethylformamide and acetonitrile, at reaction temperatures varying from 25° C to 150° C, preferably from 50° C to 150° C. The reaction pressure may be atmospheric, subatmospheric or superatmospheric. However, for convenience of conducting the reaction, the pressure is generally atmospheric. The reaction time will, of course, vary depending upon the reactants and the reaction temperature. Generally the reaction time is from 0.25 to 24 hours. The product (IV) is generally purified by conventional procedures, e.g., extraction, distillation or crystallization, before use in the acylation reaction (2).

The acylation reaction (2) is conducted by conventional procedures in the presence of an organic amine such as trialkyl amine or a pyridine compound. The reactants (IV) and (V) and the amine are generally contacted in substantially equimolar amounts in an inert organic solvent at a temperature of 0° to 100° C. Suitable inert organic solvents include ethyl acetate, methylene dichloride, dimethoxyethane, benzene, etc. The product is isolated and purified by conventional procedures such as extraction, distillation, chromatog-

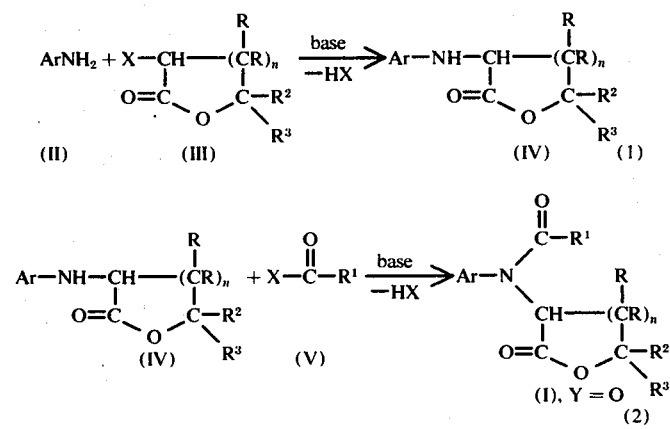

wherein Ar, R, $R^1$, $R^2$, $R^3$ and $n$ have the same significance as previously defined, and X is chloro or bromo.

The alkylation reaction (1) is conducted in the presence of a base. Suitable bases are inorganic alkali metal carbonates such as sodium carbonate or potassium carbonate. Generally, substantially equimolar amounts of reactants (II) and (III) and the base are employed. In raphy, crystallization, etc.

The lactam compounds of the invention may be prepared by cyclizing a gamma-halo or delta-halo amide (VI) in the presence of a base and subsequently acylating the gamma-lactam or delta-lactam (VII) to give the 3-(N-acyl-N-arylamino)-gamma-lactam or delta-lactam product (I), as depicted in the following equations:

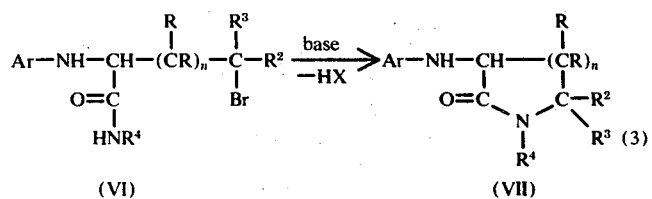

-continued

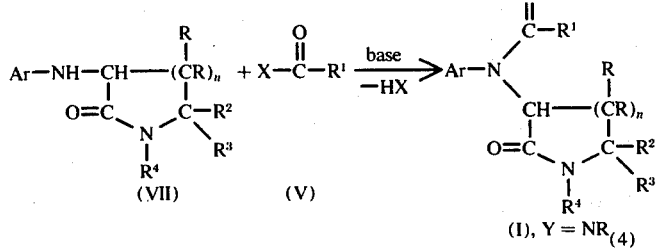

(I), Y = NR$_{(4)}$ wherein Ar, R, $R^1$, $R^2$, $R^3$, $R^4$, $n$ and X have the same significance as previously defined.

The cyclization reaction (3) is conducted by treating the gamma-halo or delta-halo amide (VI) with substantially equimolar amounts of a strong inorganic base, e.g., alkali metal alkoxides such as sodium methoxide, potassium ethoxide, etc., and alkali metal hydrides such as sodium hydride. When an alkali metal alkoxide base is employed, the reaction is preferably conducted in an alkanol solvent such as methanol and ethanol. When an alkali metal hydride base is employed, the reaction is preferably conducted in a polar non-hydric oxygenated solvent such as dimethoxyethane. The lactam product (VII) is purified by conventional procedures such as extraction, distillation, chromatography or crystallization before use in the acylation reaction (4).

The acylation reaction (4) is conducted in the presence of an organic amine base by the same procedure disclosed above for reaction (2).

The gamma-halo or delta-halo amide reactant (VI) is suitably prepared by halogenating by conventional procedures, e.g., with phosphorus tribromide or thionyl chloride, the corresponding gamma-hydroxy or delta-hydroxy amide, i.e., the compound of formula (VIII):

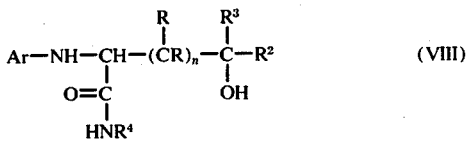

The gamma-hydroxy or delta-hydroxy amide (VIII) in turn is prepared by reacting the 3-(N-arylamino)-gamma-lactone or delta-lactone (IV) with ammonia or an amine ($H_2NR^4$) in an inert solvent at a temperature of 25° to 100° C, and subsequently purifying the product by conventional procedures.

EXAMPLES

The preparation of the compounds of the invention by the above reaction is illustrated by the following examples.

EXAMPLE 1

Preparation of
3-(N-propionyl-N-3,4-dichlorophenylamino)-gamma-butyrolactone

A reaction flask was charged with 32.4 g (0.2 mol) of 3,4-dichloroaniline and 16.5 g (0.1 mol alpha-bromo-gamma-butyrolactone. The flask was evacuated to 20 mm of Hg and then slowly heated to 110°–145° C. The reaction pressure increased to 88 mm of Hg. After maintaining at about 23 mm of Hg and 120° C for 1 hour, the reaction mixture was cooled to give a solid mixture of 3,4-dichloroaniline hydrobromide salt and 3-(N-3,4-dichlorophenylamino)-gamma-butyrolactone. The mixture was treated with methylene chloride and filtered. The filtrate was evaporated to give the lactone product [(IV), Ar=3,4-dichlorphenyl, R, $R^2$ and $R^3$=H, $n$=1 and Y=0].

A solution of 5.9 g (0.024 mol) 3-(N-3,4-dichlorophenylamino)-gamma-butyrolactone, 2.1 g (0.026 mol) pyridine and 2.4 g (0.026 mol) propionyl chloride in 110 ml ethyl acetate was heated at 45° C. After ½-hour at 45° C, thin-layer chromatographic analysis showed substantial amounts of the lactone reactant. Another 2.1 g pyridine and 2.4 g propionyl chloride were added to the reaction mixture. The reaction mixture was then heated at reflux for ½ hour, cooled, washed with water, 10% aqueous sodium bicarbonate, water; dried over magnesium sulfate and evaporated to give an oil. The oil was chromatographed on a silica gel column. The product was eluted from the column as a colorless oil with 75:25 hexane/ether. The product crystallized from ether as a white solid. The melting point and elemental analysis on the product are tabulated in Table I, as compound No. 1.

EXAMPLE 2

Preparation of
3-(N-3,4-dichlorobenzoyl-N-2,6-dimethylphenylamino-gamma-butyrolactone A slurry of 12.2 g (0.1 mol) 2,6-dimethylaniline, 16.5 g (0.1 mol) alpha-bromo-gamma-butyrolactone, 10.6 g (0.1 mol) sodium carbonate and 150 ml dimethylformamide was heated at 125°–140° C for 21 hours. The reaction mixture was then diluted with water and extracted with benzene. The benzene extracts were washed with water, dried over magnesium sulfate and evaporated to give an oil. The oil was chromatographed on a silica gel column. 3-(N-2,6-dimethylphenylamino)-gamma-butyrolactone, m.p. 85°–87° C, was eluted from the column with 50:50 hexane/ether.

A solution of 6.2 g (0.03 mol) 3-(N-2,6-dimethylphenylamino)-gamma-butyrolactone, 6.9 g (0.033 mol) 3,4-dichlorobenzoyl chloride, 2.6 g (0.033 mol) pyridine and 150 ml ethyl acetate was stirred overnight at 25° C and then at 50°–75° C for 3 hours. After cooling, the reaction mixture was washed with water, diluted with methylene chloride, washed with water, 10% aqueous sodium bicarbonate, washed with water, dried over magnesium sulfate and evaporated to give a solid residue. The residue was crystallized from ethyl ether to give the product as a colorless solid. The melting point and elemental analysis for the product is tabulated in Table I, as compound No. 2.

EXAMPLE 3

Preparation of
3-(N-chloroacetyl-N-2-methoxyphenylamino)-gamma-butyrolactone

A slurry of 12.3 g (0.1 mol) 2-methoxyaniline, 16.5 g (0.1 mol) alpha-bromo-gamma-butyrolactone, 10.6 g (0.1 mol) sodium carbonate and 150 ml dimethylformamide was stirred at 25° C for 16 hours and then at 90–100° C for 6 hours. The reaction mixture was diluted with water and extracted with benzene. The benzene extracts were washed with water, dried over magnesium sulfate and evaporated to give an oil. The oil was chromatographed on a silica gel column. 3-(N-2-methoxyphenylamino)-gamma-butyrolactone was eluted from the column with 80:20 hexane/ether.

A 5.4 g (0.044 mol) sample of chloroacetyl chloride was added dropwise to a solution of 9 g (0.044 mol) 3-(N-2-methoxyphenylamino)-gamma-butyrolactone and 3.8 g (0.048mol) pyridine in 150 ml ethyl acetate at 37°–46° C. After stirring at 46° C for 15 minutes, the reaction mixture was cooled and diluted with water. The organic layer was separated, washed with 10% aqueous sodium bicarbonate, washed with water, dried over magnesium sulfate and evaporated under reduced pressure to give the product, as a colorless solid. The melting point and elemental analysis for the product is tabulated in Table I, as compound No. 3.

EXAMPLE 4

Preparation of
1-methyl-3-(N-chloroacetyl-N-2,6-dimethylphenylamino)-gamma-butyrolactam A solution of 20.5 g (0.1 mol) 3-(N-2,6-dimethylphenyl)-gamma-butyrolactone, 4.7 g (0.15 mol) methylamine (40% solution in water) and 200 ml methanol was stirred at 25° C for 48 hours. The solvent was evaporated under reduced pressure to give an oil residue. The residue was dissolved in methylene chloride, washed with water, dried over magnesium sulfate and evaporated to give N-methyl-2-(N'-2,6-dimethylphenylamino)-4-hydroxybutyramide [ (VIII), Ar=2,6-dimethylphenyl, R, $R^2$ and $R^3$=H, N-$R^4$=NCH$_3$, n=1 ].

A solution of 13.5 g (0.05 mol) phosphorus tribromide in 5 ml methylene chloride was added dropwise at 0° C (ice bath) to a solution of 23.6 g (0.1 mol) N-methyl-2-(N'-2,6-dimethylphenylamino)-4-hydroxybutyramide and 7.9 g (0.1 mol) pyridine in 200 ml methylene chloride. After the addition was completed, the reaction mixture was stirred at 25° C for 2 hours and at reflux for 1 hour. The reaction mixture was diluted with water. The organic layer was separated, washed with water, dried over magnesium sulfate and evaporated to give the crude N-methyl-2-(N'-2,6-dimethylphenylamino)-4-bromobutyramide [ (VI), Ar=2,6-dimethylphenyl, R, $R^2$ and $R^3$=H, N-$R^4$=NCH$_3$ and n=1 ], as a glassy solid.

The crude bromo-amide was diluted with 150 ml ethanol and reacted with a solution of sodium ethoxide (prepared from 5.6 g of 43% NaH in mineral oil) in 100 ml ethanol at 25° C for about 16 hours. The reaction mixture was evaporated, dissolved in water and filtered. The aqueous filtrate was washed with petroleum ether, acidified to pH 1 with 10% hydrochloric acid, extracted with methylene chloride and evaporated to give 1-methyl-3-(N-2,6-dimethylphenylamino)-gamma-butyrolactam, as an oil.

Chloroacetyl chloride (1.8 g, 0.015 mol) was added dropwise to a stirred solution of 3 g (0.014mol) 1-methyl-3-(N-2,6-dimethylphenylamino)-gamma-butyrolactam, 1.2 g (0.015 mol) pyridine and 50 ml ethyl acetate. The reaction mixture was stirred at 25° C for about 16 hours. The reaction mixture was then diluted with water and ether. The organic layer was separated, washed with saturated aqueous sodium bicarbonate, dried over magnesium sulfate and stripped to give an oil. The oil was chromatographed on a silica gel column. The product was eluted from the column with ether. The melting point and elemental analysis on the product is tabulated in Table I, as compound No. 4.

EXAMPLE 5

Preparation of
1-allyl-3-(N-chloroacetyl-N-2,6-dimethylphenylamino)-gamma-butyrolactam A solution of 20.5 g (0.1 mol) 3-(N-2,6-dimethylphenyl)-gamma-butyrolactone, 5.9 g (0.1 mol) allylamine and 200 ml methanol was stirred at 25° C for 16 hours and under reflux for 6.5 hours. An additional 2 g of allylamine was then added and heating under reflux continued for 4.5 hours. The solvent was then evaporated under reduced pressure to give an oil residue. The residue was chromatographed on silica gel (ether/petroleum ether elution) to give 21 g of N-allyl-2-(N'-2,6-dimethylphenylamino)-4-hydroxybutyramide [ (VIII), Ar=2,6-dimethylphenyl, R, $R^2$ and $R^3$=H, N-$R^4$=NCH$_2$CH=CH$_2$, n=1 ].

A sample of 8.7 g (0.073 mol) thionyl chloride was added dropwise at 0° C (ice bath) to a solution of 17.5 g (0.067 mol) N-allyl-2-(N'-2,6-dimethylphenylamino)-4-hydroxybutyramide in 250 ml methylene chloride. After the addition was completed, the reaction mixture was stirred at 25° C for 2 hours and at a reflux until gas evolution ceased (about 12 hours). The reaction mixture was diluted with 200 ml water. The organic layer was separated, washed with water, dried over magnesium sulfate and evaporated to give the crude N-allyl-2-(N'-2,6-dimethylphenylamino)-4-chlorobutyramide [ (VI), Ar=2,6-dimethylphenyl, R, $R^2$ and $R^3$=H, N-$R^4$=NCH$_2$CH=CH$_2$ and n=1 ], as an oil.

The crude chloro-amide was diluted with 250 ml dimethoxyethane and reacted with 3.2 g of sodium hydride (50% in mineral oil). The reaction mixture was then stirred overnight at about 25° C, then filtered through Celite and washed with methylene chloride. The filtrate was evaporated and chromatographed on silica gel (ether/petroleum ether elution) to give 8.2 g of 1-allyl-3-(N-2,6-dimethylphenylamino)-gamma-butyrolactam, as an oil.

Chloroacetyl chloride (4.8 g, 0.042 mol) was added dropwise to a stirred solution of 9.4 g (0.039 mol) 1-allyl-3-(N-2,6-dimethylphenylamino-gamma-butyrolactam, 3.3 g (0.042 mol) pyridine and 100 ml ethyl acetate. The reaction mixture was stirred at 25° C for about 16 hours. The reaction mixture was then diluted with water. The organic layer was separated, washed with saturated aqueous sodium bicarbonate, dried over magnesium sulfate and stripped to give an oil. The oil was chromatographed on a silica gel column. The product (10.9 g was eluted from the column with ether. The melting point and elemental analysis on the product is tabulated in Table I, as compound No. 22.

Compound Nos. 6–21 and 23–25 of Table I were prepared by procedures similar to those of Examples 1–5.

UTILITY

The compounds of the invention are useful for controlling fungi, particularly plant fungal infections caused by Botrytis cinerea, leaf blights caused by organisms such as Erysiphe polygoni and E. chicoraciarum and other fungal infections caused by organisms such as Pythrium ultimum, Helminthosporum sativum, Fusarium moniliforme, Rhizoctonia solani, Monolinia fructicola and Uromyces phaseoli typica. However, some fungicidal compounds of the invention may be more fungicidally active than others against particular fungi.

When used as fungicides, the compounds of the invention are applied in fungicidally effective amounts to fungi and/or their habitats, such as vegetative hosts and nonvegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, wettable, inorganic diluents. Typical wetting, dispersing or emulsifying agents include, for example: the aryl and alkylaryl sulfonates and their sodium salts, alkylamide sulfonates, including fatty methyl taurides; alkylaryl polyether alcohols, sulfated higher alcohols and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLE 6

Tomato Late Blight

Compounds of the invention were tested for the control of the Tomato Late Blight organism Phytophthora infestans conidia. Five-to six-week-old tomato (variety Bonny Best) seedlings were used. The tomato plants were sprayed with a 250-ppm solution of the test compound in acetone, water and a small amount of nonionic emulsifier. The sprayed plants were then inoculated one day later with the organism, placed in an environmental chamber and incubated at 60°–68° F and 100% relative humidity for at least 16 hours. Following the incubation, the plants were allowed to dry and then were maintained at 60–80% relative humidity for approximately 7 days. The percent disease control provided by a given test compound was based on the percent disease reduction relative to untreated check plants. The compounds tested and the results are tabulated in Table II.

EXAMPLE 7

Tomato Early Blight

Compounds of the invention were tested for control of the Tomato Early Blight organism, Alternaria solani conidia. Tomato (variety Bonny Best) seedlings of 6 to 7 weeks old were used. The tomato plants were sprayed with a 250-ppm solution of the test compound in an acetone-and-water solution containing a small amount of a non-ionic emulsifier. The sprayed plants were inoculated one day later with the organism, dried and maintained at 60–80% relative humidity for about 12 days. Percent disease control was based on the percent disease development on untreated check plants. The compounds tested and the results are tabulated in Table II.

EXAMPLE 8

Celery Late Blight

Compounds of the invention were tested for the control of Celery Late Blight using celery (Utah) plants 11 weeks old. The Celery Late Blight organism was *Septoria apii*. The celery plants were sprayed with solutions of the candidate toxicant mixed with acetone, water and a nonionic emulsifier. The plants were then inoculated with the organism and placed in an environmental chamber and incubated at 66°–68° F in 100% relative humidity for an extended period of time (approximately 48 hours). Following the incubation, the plants were allowed to dry and then were maintained at a 60–80% relative humidity for approximately 14 days. The percent disease control provided by a given candidate toxicant is based on the percent disease reduction relative to untreated check plants. The results are reported in Table II.

EXAMPLE 9

Botrytis cinerea control

Compounds of the invention were tested for *Botrytis cinerea* control using detached, well-developed primary leaves of a 4–6 week old horsebean plant. The leaves were dipped into a 40-ppm solution of the test compound in acetone and water containing a small amount of a nonionic emulsifier, then taken out and placed in a petri plate lined with two pieces of filter paper. The leaves were allowed to dry while the filter paper was kept moist by adding water as required. The treated leaves were then inoculated with the spores of *Botrytis cinerea* fungus grown on potato dextrose agar plates. The plate was covered after inoculation and kept at 23.5° C. The filter-paper lining of the plate was kept saturated with water throughout the test. The rate of disease incidence was determined in 3 to 5 days, when the disease symptoms were fully evident on non-treated check leaves. The percentage disease control provided by the test compound was calculated as the percentage disease reduction based on the non-treated check leaves. The test compounds and the results are tabulated in Table II.

EXAMPLE 10

Powdery Mildew

The powdery mildew test was made using bean seedlings (var. Bountiful) with well-developed primary leaves. The pathogen was *Erysiphe polygoni*. The bean seedlings were sprayed with a 250-ppm solution of the test compound in an acetone-water mixture containing a nonionic emulsifier. The treated plants were inoculated one day after spray application of the test compound with the pathogen. The plants were then maintained in a greenhouse at a 60–80% relative humidity and at a temperature of 68°–70° F. The rate of infection on the leaves was made after about 10 days. The percent disease control provided by a given test compound was based on the disease reduction relative to untreated check plants. The results are reported in Table II.

A compound of the formula 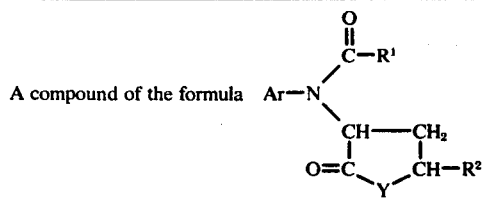

| No. | Ar | Y | R¹ | R | Melting Point, °C | Halogen Analysis Calc. | Halogen Analysis Found |
|---|---|---|---|---|---|---|---|
| 1 | 3,4-dichlorophenyl | O | —CH₂CH₃ | H | 112–114 | 23.5 | 23.1 |
| 2 | 2,6-dimethylphenyl | O | -3,4-diCl—φ | H | 151–160 | 18.8 | 22.5 |
| 3 | 2-methoxyphenyl | O | —CH₂Cl | H | 123–124 | 12.5 | 12.1 |
| 4 | 2,6-dimethylphenyl | NCH₃ | —CH₂Cl | H | 121–122 | 12.0 | 12.0 |
| 5 | phenyl | O | —CH₂Cl | H | 91–93 | 14.0 | 14.1 |
| 6 | 2,6-diethylphenyl | O | —CH₂Cl | H | 104–105 | 11.5 | 11.4 |
| 7 | 2-isopropylphenyl | O | —CH₂Cl | H | 152–154 | 12.0 | 11.3 |
| 8 | 2,6-dimethylphenyl | O | —CH₂Cl | H | 141–143 | 12.6 | 12.8 |
| 9 | 2-ethylphenyl | O | —CH₂Cl | H | 108–109 | 12.6 | 12.4 |
| 10 | 2,6-dichlorophenyl | O | —CH₂Cl | H | 172–174 | 33.0 | 31.7 |
| 11 | 3,4-dichlorophenyl | O | —CH₂Cl | H | 48–50 | 33.0 | 30.6 |
| 12 | 3,5-dichlorophenyl | 0 | —CH₂Cl | H | 143–144 | 33.0 | 31.4 |
| 13 | 2,6-diethylphenyl | O | —CH₂Cl | CH₃ | 36–37 | 11.0 | 11.0 |
| 14 | 2,6-dimethylphenyl | O | —CH₂Cl | CH₃ | 34–35 | 12.0 | 12.2 |
| 15 | 2-methyl-6-ethylphenyl | O | —CH₂Cl | H | 119–120 | 12.0 | 12.1 |
| 16 | 2-methyl-6-ethylphenyl | O | —CH₂Cl | CH₃ | 92–94 | 11.5 | 11.5 |
| 17 | 2,6-dimethylphenyl | O | —CH₂Br | H | 116–117 | 24.5 | 25.1 |
| 18 | 2,6-dimethoxyphenyl | O | —CH₂Cl | H | 148–150 | 11.3 | 11.3 |
| 19 | 2,6-dimethylphenyl | O | —CH₂CH₂Cl | H | 108–109 | 12.0 | 11.8 |
| 20 | 2,6-dimethylphenyl | NCH(CH₃)₂ | —CH₂Cl | H | 67–69 | 11.0 | 10.8 |
| 21 | 2,6-dimethylphenyl | O | —CCl=CCl₂ | H | 129–130 | 29.3 | 28.7 |
| 22 | 2,6-dimethylphenyl | NCH₂CH=CH₂ | —CH₂Cl | H | oil | 11.1 | 12.1 |
| 23 | 2,6-dimethylphenyl | NH | —CH₂Cl | H | 152–154 | 12.6 | 12.5 |
| 24 | 2,6-dimethylphenyl | N(3-CH₃—4-Cl) φ | —CH₂Cl | H | 137–140 | 17.5 | 17.1 |
| 25 | 2,6-dimethyl henyl | NCH₃ | 4-Cl—φ | H | 169–174 | 9.93 | 10.3 |

φ = phenyl

TABLE II

| Compound No. | % Control Tomato Late Blight | Tomato Early Blight | Celery Late Blight | *Botrytis cinerea* | Bean Powdery Mildew |
|---|---|---|---|---|---|
| 1 | — | — | 73 | — | — |
| 2 | — | — | 27 | — | — |
| 3 | 23 | 98 | — | — | 44 |
| 4 | — | 92 | — | — | — |
| 5 | — | 63 | — | — | — |
| 6 | 39 | — | — | 56 | — |
| 7 | — | 56 | 39 | — | — |
| 8 | 100 | 44 | — | — | — |
| 9 | 35 | 21 | — | — | — |
| 10 | — | 27 | 33 | — | — |
| 11 | — | 81 | 60 | — | — |
| 12 | — | — | — | — | — |
| 13 | 21 | — | — | — | — |
| 14 | 100 | — | — | — | — |
| 15 | 95 | — | 23 | — | — |
| 16 | — | — | — | 17 | — |
| 17 | — | — | 27 | — | — |
| 18 | — | — | — | 42 | — |
| 19 | — | — | 23 | 33 | — |
| 20 | — | — | — | — | 69 |
| 21 | 44 | — | 23 | — | — |
| 22 | — | — | 23 | — | — |
| 23 | — | — | 35 | — | — |
| 24 | — | 63 | 18 | — | — |
| 25 | — | 23 | — | — | — |

What is claimed is:

1. A compound of the formula

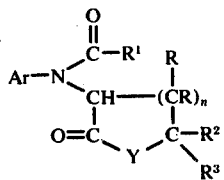

wherein Ar is phenyl or phenyl substituted with 1 to 3 of the same or different substituents selected from fluoro, chloro, bromo, alkyl of 1 to 4 carbon atoms, alkoxy of 1 to 4 carbon atoms or nitro; R is hydrogen or alkyl of 1 to 6 carbon atoms; $R^1$ is alkyl of 1 to 6 carbon atoms, haloalkyl of 1 to 3 carbon atoms and 1 to 5 of the same or different halogen selected from fluoro, chloro, or bromo, halovinyl of 1 to 3 of the same or different halogens selected from fluoro, chloro or bromo, phenyl, or phenyl substituted with 1 to 3 of the same or different substituents selected from trifluoromethyl, trichloromethyl, fluoro, chloro, bromo, alkyl of 1 to 4 carbon atoms, alkoxy of 1 to 4 carbon atoms or nitro; $R^2$ is hydrogen or alkyl of 1 to 6 carbon atoms; $R^3$ is hydrogen or alkyl of 1 to 6 carbon atoms; n is 1 or 2; and Y is $N-R^4$ wherein $R^4$ is hydrogen, alkyl of 1 to 6 carbon atoms, alkenyl of 3 to 6 carbon atoms, phenyl or phenyl substituted with 1 to 3 of the same or different substituents selected from trifluoromethyl, trichloromethyl, fluoro, chloro, bromo, alkyl of 1 to 4 carbon atoms, alkoxy of 1 to 4 carbon atoms or nitro.

2. The compound of claim 1 wherein R, $R^2$ and $R^3$ are hydrogen and, $R^1$ is alkyl.

3. The compound of claim 1 wherein R, $R^2$ and $R^3$ are hydrogen and, $R^1$ is haloalkyl of 1 to 3 carbon atoms and of 1 to 2 chloro or bromo.

4. The compound of claim 1 wherein R, $R^2$ and $R^3$ are hydrogen, $R^1$ is chloromethyl or bromomethyl, Ar is 2,6-dialkylphenyl, n is 1 and $R^4$ is alkyl.

5. The compound of claim 1 wherein R, $R^2$ and $R^3$ are hydrogen, $R^1$ is phenyl or phenyl substituted with 1 to 2 of the same or different substituents selected from fluoro, chloro, bromo or alkyl of 1 to 6 carbon atoms, and $R^4$ is alkyl.

6. A method for the control of fungi which comprises contacting said fungi or their habitats with a fungicidally effective amount of the compound of claim 1.

7. The method of claim 6 wherein R, $R^2$ and $R^3$ are hydrogen and $R^1$ is alkyl.

8. The method of claim 6 wherein R, $R^2$ and $R^3$ are hydrogen, and $R^1$ is haloalkyl of 1 to 3 carbon atoms and of 1 to 2 chloro or bromo.

9. The method of claim 6 wherein R, $R^2$ and $R^3$ are hydrogen, $R^1$ is chloromethyl or bromomethyl, Ar is 2,6-dialkylphenyl, n is 1 and $R^4$ is alkyl.

10. The method of claim 6 wherein R, $R^2$ and $R^3$ are hydrogen, $R^1$ is phenyl or phenyl substituted with 1 to 2 of the same or different substituents selected from fluoro, chloro, bromo or alkyl of 1 to 6 carbon atoms, and $R^4$ is alkyl.

11. A fungicidal composition comprising a fungicidally effective amount of the compound of claim 1 and a biologically inert carrier.

12. The composition of claim 11 wherein R, $R^2$ and $R^3$ are hydrogen, and $R^1$ is alkyl.

13. The composition of claim 11 wherein R, $R^2$ and $R^3$ are hydrogen, and $R^1$ is haloalkyl of 1 to 3 carbon atoms and of 1 to 2 chloro or bromo.

14. The composition of claim 11 wherein R, $R^2$ and $R^3$ are hydrogen, $R^1$ is chloromethyl or bromomethyl, Ar is 2,6-dialkylphenyl, n is 1 and $R^4$ is alkyl.

15. The composition of claim 11 wherein R, $R^2$ and $R^3$ are hydrogen, $R^1$ is phenyl or phenyl substituted with 1 to 2 of the same or different substituents from fluoro, chloro, bromo or alkyl of 1 to 6 carbon atoms, and $R^4$ is alkyl.

* * * * *